US00PP13121P2

(12) United States Plant Patent
Bubani

(10) Patent No.: US PP13,121 P3
(45) Date of Patent: Oct. 22, 2002

(54) JAPANESE PLUM TREE NAMED 'APHRODITE'

(76) Inventor: Giovanni B. Bubani, 5490 E. Liberty Ave., Fresno, CA (US) 93727

( * ) Notice: Subject to any disclaimer, the term of this patent is extended or adjusted under 35 U.S.C. 154(b) by 0 days.

(21) Appl. No.: 09/727,686

(22) Filed: Dec. 4, 2000

(65) Prior Publication Data

US 2002/0069436 P1 Jun. 6, 2002

(51) Int. Cl.[7] ..... A01H 5/00
(52) U.S. Cl. ..... Plt./184
(58) Field of Search ..... Plt./184

*Primary Examiner*—Bruce R. Campell
*Assistant Examiner*—Anne Marie Grünberg
(74) *Attorney, Agent, or Firm*—Burns, Doane, Swecker & Mathis, LLP

(57) ABSTRACT

A new and distinct cultivar of Japanese Plum tree (*Prunus salicina*) is provided that forms large well-colored fruit of excellent flavor that is larger in size than that of the 'Santa Rosa' cultivar. The fruit flavor is generally comparable to that of the 'Santa Rosa' cultivar. The fruit ripens a few days later than the 'Santa Rosa' cultivar and is firmer than that of the 'Santa Rosa' cultivar at commercial maturity. The tree is a regular bearer and has exhibited greater fruit productivity than the 'Santa Rosa' cultivar.

1 Drawing Sheet

BOTANICAL/COMMERCIAL CLASSIFICATION

*Prunus salicina*/Japanese Plum.

VARIETAL DENOMINATION cv. 'Aphrodite'.

SUMMARY OF THE INVENTION

The present invention is directed to a new and distinct Japanese Plum (i.e., *Prunus salicina*) cultivar that originated near Sanger, Calif. during the course of a controlled breeding program. More specifically, during February, 1991, the 'Shayna' cultivar (non-patented in the United States) was crossed with the 'Santa Rosa' cultivar (non-patented in the United States). The parentage of the new cultivar can be summarized as follows:

'Shayna'×'Santa Rosa'.

Eighty seeds were produced from this cross and were planted near Sanger, Calif. during 1992 and germinated and grew to yield seedling plants during 1992 and 1993. During the 1994 growing season the seedlings produced a substantial quantity of fruit and were studied in detail. A single plant of new cultivar was selected and was carefully preserved.

It was found that the new Japanese Plum cultivar of the present invention exhibits the following combination of characteristics:

(a) Forms large well-colored fruit of excellent firmness and flavor that is larger in size than that of the 'Santa Rosa' cultivar,
(b) Forms fruit that ripens a few days after that of the 'Santa Rosa' cultivar, and
(c) Is a regular bearer with greater fruit productivity than the 'Santa Rosa' cultivar.

During the spring of 1995 the new cultivar of the present invention was first asexually propagated by grafting onto one year-old 'Marianna' plum rootstock (nonpatented in the United States) near Sanger, Calif. The resulting asexually reproduced trees produced few fruit in 1996, and produced the first significant fruit crop in 1997. Such significant fruiting has continued in each year thereafter. It has been confirmed that the characteristics of the new cultivar are strictly transmitted to the next generation following such asexual propagation.

The new cultivar of the present invention can be readily distinguished from its 'Santa Rosa' cultivar parent by the formation of generally larger fruit, the formation of firmer fruit at commercial maturity, overall greater fruit productivity, and a later fruit maturity by a few days. Additionally, the new cultivar can be readily distinguished from its 'Shayna' cultivar parent by differences in ripening time, fruit attachment to the stone, fruit size, fruit color, productivity, and pollination requirements. The 'Shayna' cultivar commonly ripens much later during the first week of August, is complete freestone, forms larger fruit that is lighter purple with a lesser coloration of the fruit surface, is less productive and an erratic bearer, and bears self-incompatible flowers.

The new cultivar of the present invention has been named 'Aprodite'.

BRIEF DESCRIPTION OF THE PHOTOGRAPH

The accompanying photograph shows specimens of the foliage and fruit of the new cultivar at maturity as depicted in color as nearly true as it is reasonably possible to make the same in a color illustration of this character. The plant was grown at Sanger, Calif.

DETAILED BOTANICAL DESCRIPTION

The following is a detailed description of a four year-old tree of the new cultivar while grafted on Nemaguard (non-patented in the United States) peach rootstock and growing near Sanger, Calif. The tree spacing was 5.25 meters between rows and 2.7 meters between trees within the row. The description is based upon fruit produced during the year 2000. Color identification is with reference to The R.H.S.

Colour Chart of The Royal Horticultural Society, London (1995).

Botanical classification: *Prunus salicina,* cv. 'Aphrodite'.

Tree:

*Size.*—Approximately 4.8 to 5.0 meters in height including approximately 0.9 to 1.5 meters of current season's growth, and approximately 2.6 to 2.7 meters in width.

*Vigor.*—Good.

*Productivity.*—Good fruit density, regular bearer, and produces fruit on both one year-old and more mature spurs. Observations to date indicate that the new cultivar is a more regular bearer than its 'Santa Rosa' parent.

*Growth habit.*—Upright to slightly spreading.

*Hardiness.*—Observed to be hardy under normal climatic conditions found in the Central San Joaquin Valley fruit production area of California.

*Trunk.*—When measured approximately 45 cm above the ground at the point where the new cultivar is grafted onto the rootstock, the diameter of the rootstock is approximately 9.5 to 10 cm and the diameter of the new cultivar is approximately 11.5 to 14 cm. The plum/peach union is very strong with a slight overgrowth of the peach rootstock by the new cultivar top. This type of overgrowth is common when a plum cultivar of *Prunus salicina* is grafted onto a peach rootstock. The bark texture is relatively coarse and bears a substantial quantity of scarfskin. The bark bears moderately large lenticels that commonly range in height from approximately 2 to 3 mm and in width from approximately 3 to 10 mm. The lenticel surfaces commonly bear substantial brown callous near Brown Group 165B. The bark coloration commonly ranges from charcoal grey, Grey Group 201A, to tan-brown, Greyed-Orange Group 165A.

Branches:

*Size.*—Average for the species. Larger branches known as "spreader" branches are commonly somewhat upright and commonly range in diameter from approximately 12 to 23 mm. Smaller fruiting branches known as "hanger" branches are commonly positioned at or below horizontal to the ground and commonly range in diameter from approximately 7 to 12 mm. Such measurements are provided for four year-old trees at the base of the branches at the point of attachment to the primary scaffolds.

*Texture.*—The surface of two year-old and older wood is somewhat furrowed with numerous light-colored lenticels. The current season's shoots are relatively smooth and are substantially glabrous.

*Internode length.*—Typical for the species and commonly ranges from approximately 19 to 30 mm between nodes on the shoots of the current season.

*Color.*—Mature shoots are dark brown, Brown Group 200B, and frequently display much light growth cracks of Grey-Brown Group 199B. The current season's shoots are medium green, Yellow-Green Group 144B when young and darken with maturity to Yellow-Green Group 152A. The shoot tips commonly are bright Yellow-Green Group 144B with some bronzing of Yellow-Green Group 152D.

Leaves:

*Size.*—Medium, leaves present on a vigorous upright current season's growth commonly range from approximately 14.1 to 15.4 cm in length and approximately 5 to 6.7 cm in width. The leaf thickness is average for the species.

*Configuration.*—Obovate and at times only slightly obovate. The leaf tip narrows at the apex to an acute form and ofter twists to the side.

*Color.*—On the upper surface dark green, Green Group 137A to 137C, and on the lower surface a lighter green, Green 138A to 138B.

*Margins.*—Slightly undulate and finely crenate with numerous moderately regular crenations. The crenations are small in size and single to double in form.

*Petioles.*—Medium in size, approximately 19 to 21 mm in length and approximately 1.5 to 2 mm in thickness. The surface generally is glabrous, but commonly bears moderate pubescence on the surface of two ridges subtending the petiole groove. The coloration is Yellow-Green Group 145B with some slight darkening along the petiole groove.

*Glands.*—Small in size and commonly vary from 2 to 6 in number. The leaf glands are most frequently reniform; however, 1 to 2 of the glands present on the petiole can approach a globose configuration. Most frequently, approximately 2 to 4 glands can be found on the petiole at a location just below the base of the leaf margin. These petiole glands are usually borne on short stalks and are reniform with the exception of the most basal one or two glands that approach a globose configuration. The glands are alternate in position. Additionally, one or two glands can often be found on the basal edges of the leaf margins. These glands are commonly reniform. The glands are shiny green in coloration, Yellow-Green Group 144B and have brownish centers that become darker with advancing maturity.

*Stipules.*—Numerous leaf stipules are formed that commonly are approximately 6 to 11 mm in length. Such stipules are linear lanceolate in configuration with serrate margins. The coloration of stipules is medium green, Yellow-Green Group 144B, when young and becomes darker with age. Often the stipules are persistent and remain well into the growing season.

Flower buds:

*Size.*—Small to medium, plump and slightly appressed to the bearing stem.

*Form.*—Conic.

*Scales.*—Very slightly pubescent primarily along the scale margins.

*Color.*—Dark brown, Greyed-Orange Group 165A.

Flowers:

*Date to bloom.*—Early in relation to other cultivars of *Prunus salicina*. Full bloom was Mar. 22, 2000. First bloom was approximately 5 days earlier on Mar. 17, 2000.

*Size.*—Medium with the diameter of a fully open bloom commonly ranging from 18 to 23 mm.

*Quantity.*—Abundant in the 2000 growing season with the number of flower buds per node ranging from 1 to 4, and most frequently 2.

*Petals.*—Medium in size with the petal length commonly ranging from 9 to 11 mm and the petal width commonly ranging from 7 to 9 mm. The petal number is 5 per flower. The form is variable and ranges from slightly ovate to slightly obovate. The coloration is white, White Group 155B. The margins are moderately undulate especially over the petal apices. The claw is short in length and truncate in configuration.

*Pedicel.*—Variable, and commonly measures approximately 5 to 8 mm in length and approximately 1 mm in thickness. The surface commonly is glabrous. The coloration is pale green, Yellow-Green Group 145B.

*Nectaries.*—Dark orange, Greyed-Orange Group 164A with darkening and increased dullness with progressing maturity.

*Calyx and sepals.*—The calyx surface is glabrous and green, Green Group 142B, at the base, and green-brown, Yellow-Green Group 152D between the calyx base and the base of the sepals. The sepal surfaces are glabrous and the sepal margins are finely serrate. The sepals are medium in size and conic in configuration. The exterior sepal coloration is Green Group 142B.

*Stamens.*—The anthers are average in size and yellow-gold, Yellow Group 13A, in coloration. The filament length is variable and commonly ranges from approximately 3 to 10 mm. The filament coloration is white, White Group 155B.

*Pollen.*—Produced in abundance and Yellow-Orange Group 14B in coloration.

*Pistils.*—Commonly longer than the shortest stamens and shorter than the longest stamens. The length commonly ranges from approximately 7 to 8 mm including the ovary. The style commonly is pale yellow-green, Yellow-Green Group 150C, in coloration. The ovary is shiny green, Green Group 142A, in coloration. The pistil surface is glabrous.

Fruit: The fruit is described at full commercial maturity.

*Date of maturity.*—Early maturing. The date of the first pick in 2000 was June 23$^{rd}$. The duration of maturity was approximately two weeks. The date of the last pick in 2000 was July 5$^{th}$. For comparative purposes the parent 'Santa Rosa' cultivar had a first pick date in 2000 of June 20$^{th}$ and a last pick date in 2000 of June 30$^{th}$.

*Size.*—Large and relatively uniform especially for the early season of maturity. The cheek diameter commonly ranges from approximately 59 to 66 mm, the suture diameter from approximately 57 to 66 mm, and the axial diameter from approximately 63 to 70 mm. The size is substantially larger than that of the 'Santa Rosa' cultivar parent even with a greater crop when evaluating adjacent comparative trees of the same age.

*Configuration.*—Variable from oval to slightly ovate in lateral aspect. Generally globose in apical aspect. Most frequently symmetrical or nearly symmetrical.

*Suture.*—Commonly appears as a line approximately 2 to 3 mm in width. The line is not depressed or is only slightly depressed at or near the apical and mid-fruit areas. The suture deepens and narrows slightly over the basal shoulder with slight clefting within the cavity basin. Commonly no stitching or callousing is present along the suture line. The suture tends to be moderately darker in coloration when compared to the surrounding skin coloration. The suture coloration is dark red-purple, Red-Purple Group 59B and 59C.

*Ventral surface.*—Quite smooth in the substantial absence of lipping.

*Stem cavity.*—Relatively small and commonly ranges from 17 to 20 mm in length, 14 to 18 mm in width, and approximately 7 to 12 mm in depth. Generally oval in configuration and tends to be more extended on the ventral suture side. Sometimes a small amount of skin checking is displayed within the cavity basin or over the basal shoulders.

*Base.*—Slightly variable in configuration and most frequently is rounded, but occasionally is truncate. The base is most frequently truncate to the fruit axis.

*Apex.*—Generally rounded and only slightly raised at the pistil point. The pistil point is variable and ranges from apical to slightly oblique.

*Stem.*—Short, and commonly is approximately 7 to 9 mm in length and approximately 1.5 to 2 mm in thickiness at mid-stem. The coloration commonly light green, Yellow-Green Group 144B to 144C. When the fruit is mature, at times brown areas of Grey-Brown Group 199A to 199B are present on most stems.

Fruit skin:

*Thickness.*—Typical for a plum.

*Texture.*—Glabrous.

*Flavor.*—Acidic.

*Tenacity.*—Tenacious to the flesh at commercial maturity.

*Tendency to crack.*—No tendency to split or crack has been observed.

*Color.*—Variable with approximately 75 to 95 percent of the surface bearing red coloration at full maturity. There is a grayish waxy bloom over the entire surface. With the exterior bloom intact, the skin coloration commonly ranges from rose-purplish, Greyed-Purple Group 186B to darker purple, Greyed-Red Group 182A, with a moderate amount of variability within this range. When the bloom is removed, the skin coloration commonly ranges from medium red, Greyed-Red Group 179A to darker red-purple, Greyed-Purple Group 185A, with a moderate amount of variability within this range. Numerous light colored dots and speckles commonly are present apically and over the lateral shoulders. A yellow ground coloration commonly is present over approximately 5 to 25 percent of the surface. Such ground coloration commonly ranges from a clean cream-yellow, Yellow Group 10B, to yellow-green, Yellow-Green Group 154D, on more immature fruit. The skin coloration is generally comparable to that of the 'Santa Rosa' cultivar parent at maturity; however, the fruit of the new cultivar tends to color somewhat earlier.

Fruit flesh:

*Color.*—Uniform light yellow to yellow-cream, near Greyed-Orange Group 163C to 163D. The flesh darkens somewhat at the center around the pit cavity. No red coloration is present in the flesh.

*Firmness.*—Firmer than that of the 'Santa Rosa' cultivar parent at commercial maturity.

*Texture.*—Smooth-textured.

*Juice production.*—Moderately juicy and firm at commercial maturity. As the fruit approaches tree-ripe maturity, the flesh becomes very juicy.

*Ripening.*—Ripens and softens first over the basal shoulders.

*Flavor.*—Excellent and closely resembles that of the 'Santa Rosa' cultivar parent. As with the 'Santa Rosa' cultivar parent, the flesh areas adjacent the skin and the stone tend to be rather acidic.

*Aroma.*—Moderate in intensity and very pleasant.

*Fibers.*—A few relatively short light-colored fibers are present throughtout the flesh.

Stone:

*Freeness.*—The stone attachment has been found to be variable from year to year. Often the stone is a clingstone and is tightly attached to the fruit throughout. In some years, however, the stone is less tightly attached with fibers only clinging to the dorsal and ventral suture areas.

*Size.*—Medium to large, the length ranges from approximately 29 to 32 mm, the width from approximately 20 to 25 mm, and the thickness from approximately 10 to 13 mm.

*Fibers.*—Numerous short to medium length fibers are tightly attached to the surface of the stone both laterally and along the sutures.

*Configuration.*—Quite irregular, but generally oval.

*Base.*—Heavily eroded and distinctly notched, the base angle is most frequently very slightly oblique to the stone axis, the basal area tapers somewhat into a broad neck and is frequently moderately ridged and furrowed.

*Hilum.*—Medium in size, generally oval in configuration, and heavily eroded with no collar.

*Apex.*—Generally rounded with a sharp tip.

*Sides.*—Variable from equal to slightly unequal.

*Surface.*—Irregular and roughened with many small ridges and furrows, and commonly with one large distinct groove that is present laterally from approximately 4 to 5 mm below and roughly parallel to the ventral edge which eventually converges with the ventral edge both apically and basally.

*Ventral edge.*—Somewhat irregular and slightly eroded, approximately 1.5 to 2 mm in width at mid-suture, and with a relatively strong wing throughout the length.

*Dorsal edge.*—Very irregular with a deep groove ranging from approximately 1 to 1.5 mm in width at mid-suture that extends from the base to the apex along the suture and narrows in width at both ends. Numerous tooth-like ridges sometimes are present along the edges of the groove especially at mid-suture and over the apical shoulder. Is moderately eroded over the basal shoulder area.

*Color.*—Prior to drying is brown-orange, Greyed-Orange Group 167C, and drys to light tan brown, Greyed-Orange Group 165D.

*Tendency to split.*—None observed to date.

Use: Fresh market.

Although the new 'Aphrodite' cultivar of Japanese Plum tree possesses the above-described characteristics at Sanger, Calif., it is to be expected that variations of the usual type and magnitude may appear that are caused by differences in growing conditions, fertilization, pruning, pest control and other horticultural practices when the new cultivar is grown in different environments.

I claim:

1. A new and distinct Japanese Plum tree having the following combination of characteristics:

(a) forms large well-colored fruit of excellent firmness and flavor that is larger in size than that of the 'Santa Rosa' cultivar, (b) forms fruit that ripens a few days after that of the 'Santa Rosa' cultivar, and (c) is a regular bearer with greater fruit productivity than that of the 'Santa Rosa' cultivar;

substantially as herein shown and described.

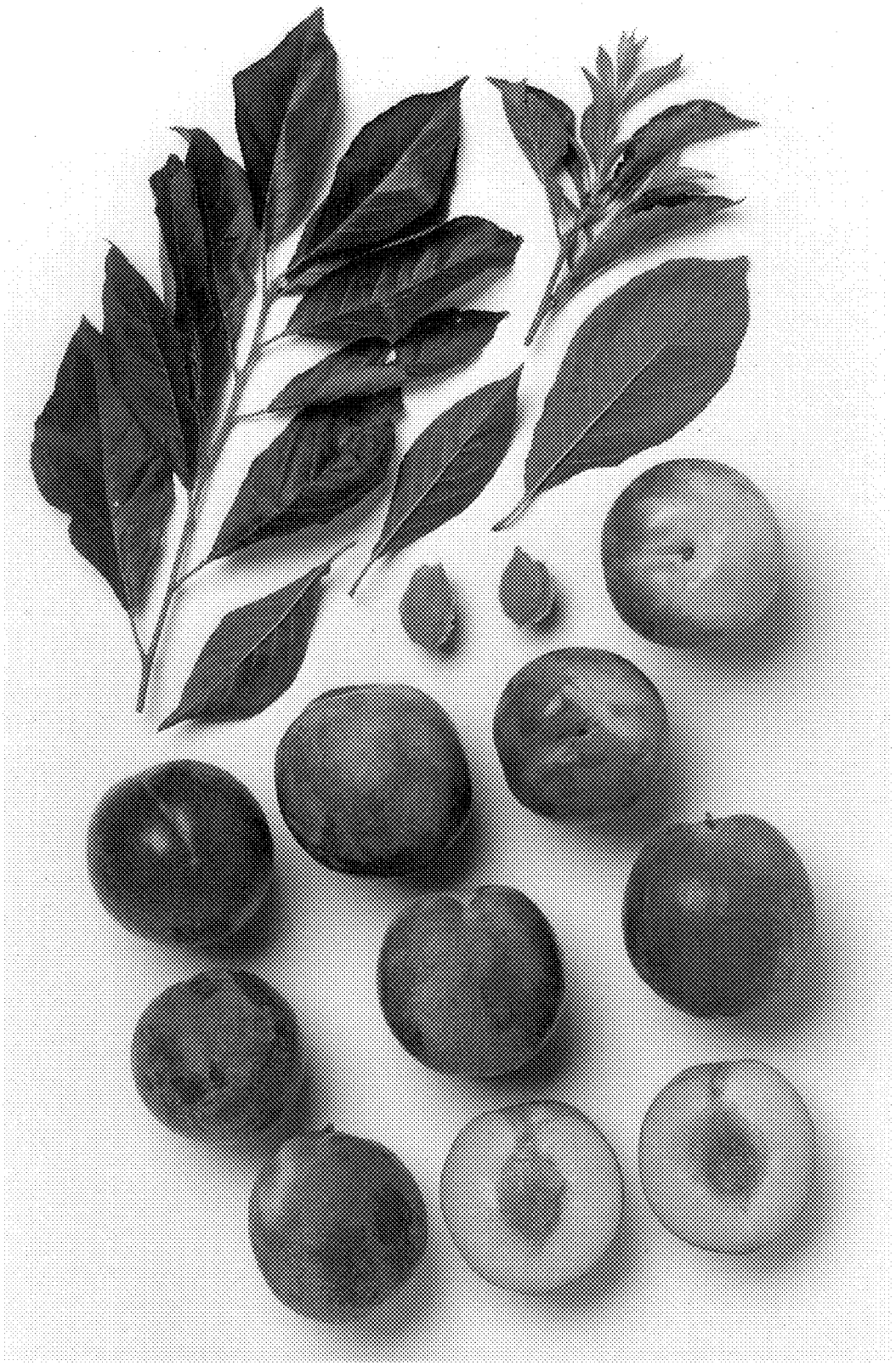

* * * * *